(12) United States Patent
Hwang et al.

(10) Patent No.: US 8,133,301 B2
(45) Date of Patent: Mar. 13, 2012

(54) POROUS NANOHYBRID MATERIALS FORMED BY COVALENT HYBRIDIZATION BETWEEN METAL-ORGANIC FRAMEWORKS AND GIGANTIC MESOPOROUS MATERIALS

(75) Inventors: Young Kyu Hwang, Daejeon (KR); Jong San Jang, Daejeon (KR); You Kyoung Seo, Busan (KR); Ji Woong Yoon, Seoul (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 468 days.

(21) Appl. No.: 12/425,039

(22) Filed: Apr. 16, 2009

(65) Prior Publication Data

US 2010/0043636 A1    Feb. 25, 2010

(30) Foreign Application Priority Data

Apr. 17, 2008    (KR) .................. 10-2008-0035621

(51) Int. Cl.
*B01D 53/02*    (2006.01)
(52) U.S. Cl. ............. 95/27; 95/90; 95/130; 95/138; 95/139; 95/143; 95/144; 96/108
(58) Field of Classification Search ............. 95/90, 127, 95/130, 138, 139, 143, 144; 534/15, 16; 556/9, 400; 96/108
See application file for complete search history.

(56) References Cited

U.S. PATENT DOCUMENTS

| | | | |
|---|---|---|---|
| 6,506,485 B1 | 1/2003 | Pinnavaia et al. | |
| 6,680,013 B1 * | 1/2004 | Stein et al. | 264/44 |

OTHER PUBLICATIONS

Fan, J. et al., "Low-Temperature Strategy to Synthesize Highly Ordered Mesoporous Silicas with Very Large Pores," J. Am. Chem. Soc., 2005, 127, pp. 10794-10795.
Zhang, Q. et al., "Assembly of quantum dots-mesoporous silicate hybrid material for protein immobilization and direct electrochemistry," 2007, Biosensors & Bioelectronics, 23, pp. 695-700.
Kitagawa, S. et al., "Functional Porous Coordination Polymers," 2004, Angew.Chem. Int. Ed., 43, pp. 2334-2375.
James, S., "Meta-organic frameworks," 2003, Chem. Soc. Rev., pp. 276-288.
Cheestham, A. et al., "There's Room in the Middle," 2007, Science, vol. 318, pp. 58-59.

* cited by examiner

*Primary Examiner* — Duane Smith
*Assistant Examiner* — Christopher P Jones
(74) *Attorney, Agent, or Firm* — Fredrikson & Byron, PA

(57) ABSTRACT

Disclosed herein is a nanoporous hybrids formed by covalent bonding between a crystalline organic-inorganic hybrid and a gigantic mesoporous metal oxide, containing organic groups on the surface thereof, having a size of 10 nm or more. Since the covalently-bonded hybrid nanoporous composite has a large surface area, a multiple microporous structure, a large pore volume and includes an organic-inorganic hybrid having backbone flexibility, the covalently-bonded hybrid nanoporous composite can be used as materials for storing liquids and gases, such as hydrogen, methane and the like, and can be used as adsorbents, separating materials, catalysts, and the like. Further, the covalently-bonded hybrid nanoporous hybrids can be used in the application fields of biomolecule supporting, drug delivery, harmful material removal, nanoparticle supporter, sensors, catalysis, adsorbents, fluorescent materials, solar cells, and the like.

14 Claims, 6 Drawing Sheets

(a)MCF-CN, (b)MCF-COOH, (c)MCF-COOH-CuBTC, (d)CuBTC

POROUS NANOHYBRID MATERIALS FORMED BY COVALENT HYBRIDIZATION BETWEEN METAL-ORGANIC FRAMEWORKS AND GIGANTIC MESOPOROUS MATERIALS

CROSS-REFERENCES TO RELATED APPLICATION

This patent application claims the benefit of priority under 35 U.S.C. §119 of Korean Patent Application No. 10-2008-0035621 filed on Apr. 17, 2008, the contents of which are incorporated herein by reference.

BACKGROUND OF THE INVENTION

1. Field of the Invention

The present invention relates to covalent bonded nanoporous hybrids and their applications thereof, and, more particularly, to a nanoporous hybrids formed by covalent bonding between a crystalline organic-inorganic hybrid having micropore and gigantic mesoporous materials, containing organic groups on the surface thereof, having a size of 10 nm or more. Since the covalent bonded nanoporous hybrids of the present invention has a large surface area, a multiple pore structure, a large pore volume and includes an organic-inorganic hybrid having backbone flexibility, it can be used as materials for gas storages and liquids, adsorbents, catalysts, membranes, magnetic materials, sensors, photoluminescence, photovoltaic and the like.

2. Description of the Related Art

To date, gigantic mesoporous materials (or mesoporous cellular foams (MCFs)) having mesopores of 10 nm or more have been synthesized using a surfactant and TMB (1,3,5-trimethylbenzene), which is a lipophilic additive, under an acidic condition by an electric heating-type hydrothermal synthesis method [U.S. Pat. No. 6,506,485; *J. Am. Chem. Soc.*, 127, 10794-10795 (2005)]. Recently, attempts to prepare gigantic mesoporous materials under weakly-acidic and neutral conditions of a pH ranging from 4 to 7 by an electric heating method have been made [*Small*, 1, 744-753 (2005); *Chem. Mater.*, 19, 3041-3051 (2007)]. Further, a method of producing MCF-$NH_2$, which is a gigantic mesoporous material including an organic functional group, by introducing —$NH_2$ group onto the surface of micropores of MCF through covalent bonding between a hydroxy group (—OH) located on the surface of a preformed gigantic mesoporous material and an organic silane, such as aminopropyltriethoxysilane (APTES), was reported [*Biosensors and Bioelectronics*, 23, 695-700(2007)]. Further, a gigantic mesoporous material of 10 nm or more was produced using both a surfactant and a pore expander during the synthesis of a general mesoporous material, such as MCM-41, SBA-15 or the like.

Meanwhile, a porous organic-inorganic hybrid is defined as a porous organic-inorganic polymeric coordination compound in which a central metal ion is bonded with organic ligands. Further, the porous organic-inorganic hybrid is a crystalline compound having a backbone structure including all organic and inorganic matter and having a molecular sized or nanosized porous structure. The porous organic-inorganic hybrid, which is a term having a wide meaning, is generally referred to as a porous coordination polymer [reference: *Angew. Chem. Int. Ed*, 43, 2334 (2004)] or a metal-organic framework (MOF) [reference: *Chem. Soc. Rev.*, 32, 276 (2003)]. In particular, since this porous organic-inorganic hybrid has a high surface area and molecular-sized or nanosized pores, the porous organic-inorganic hybrids can be used as adsorbents, gas storage materials, sensors, drug delivery materials, catalysts and catalytic supports, and can also be used to form guest molecules having a size smaller than that of a pore into clathrates or to separate molecules having a size larger than that of a pore. Therefore, recently, research on the porous organic-inorganic hybrid has been actively conducted [*Chem. Soc. Rev.*, 37, 191, (2008)]. In addition to the porous organic-inorganic hybrid, since a nonporous organic-inorganic polymeric coordination compound (or a nonporous organic-inorganic hybrid (NOITH)), such as magnesium tartrate or the like, has unique magnetic and optical properties, research on the nonporous organic-inorganic polymeric coordination compound has been conducted [*Science*, 318, 58, (2007)].

Methods of producing the gigantic mesoporous material and porous organic-inorganic hybrid and applications thereof have been very well known, but a nanoporous hybrids having the properties of both the gigantic mesoporous material and porous organic-inorganic hybrid has never been reported. Since the gigantic mesoporous material accelerates a diffusion phenomenon due to the large-sized pores thereof and the porous organic-inorganic hybrid has various characteristics, such as ultra-porosity, high surface area, metal framework structure, etc., this novel nanoporous hybrids including the gigantic mesoporous material and porous organic-inorganic hybrid are expected to exhibit new functionalities which have not yet been able to be discovered in the fields of storage materials, adsorbents, catalysts, membranes, and the like, and is expected to bring about the synergistic effects of the two materials.

SUMMARY OF THE INVENTION

Accordingly, the present invention has been made keeping in mind the above problems occurring in the prior art, and an object of the present invention is to provide a novel nanoporous hybrids produced by covalent-bonding a crystalline organic-inorganic hybrid with a gigantic mesoporous material which has a size of 10 nm and includes organic functional groups on the surface thereof. The covalently-bonded nanoporous material can be used as materials for storing liquids and gases, such as hydrogen, methane and the like, and can also be used as adsorbents, separating materials, catalysts, and the like.

The present inventors have made efforts to solve the conventional problems and to accomplish the above object. As a result, they produced a novel covalent bonded nanoporous hybrids through the following processes: in producing a gigantic mesoporous cellular material (MCF) including organic functional groups, preparing surface-functionalized MCF-CN using an organosilane compound having a functional group, such as —CN, —SH, or the like, as a silicon source; preparing MCF-$CO_2$H in which —$CO_2$H group is functionalized on the surface of MCF by oxidizing the MCF-CN; and mixing the MCF-$CO_2$H with a crystalline organic-inorganic hybrid precursor and then hydrothermally-synthesizing the mixture.

Since the ultraporous organic-inorganic nanoporous hybrids of the present invention have advantages of both a crystalline organic-inorganic hybrid and a gigantic mesoporous material, it can be widely used as catalysts, carriers, adsorbents, gas storage materials, nanoreactors, chemical delivery materials, and the like.

BRIEF DESCRIPTION OF THE DRAWINGS

The above and other objects, features and advantages of the present invention will be more clearly understood from the following detailed description taken in conjunction with the accompanying drawings, in which:

FIG. 1 is a graph showing nitrogen adsorption isothermal curves of nanoporous materials prepared in Examples 1 and 6.

DESCRIPTION OF THE PREFERRED EMBODIMENTS

Figure 1:
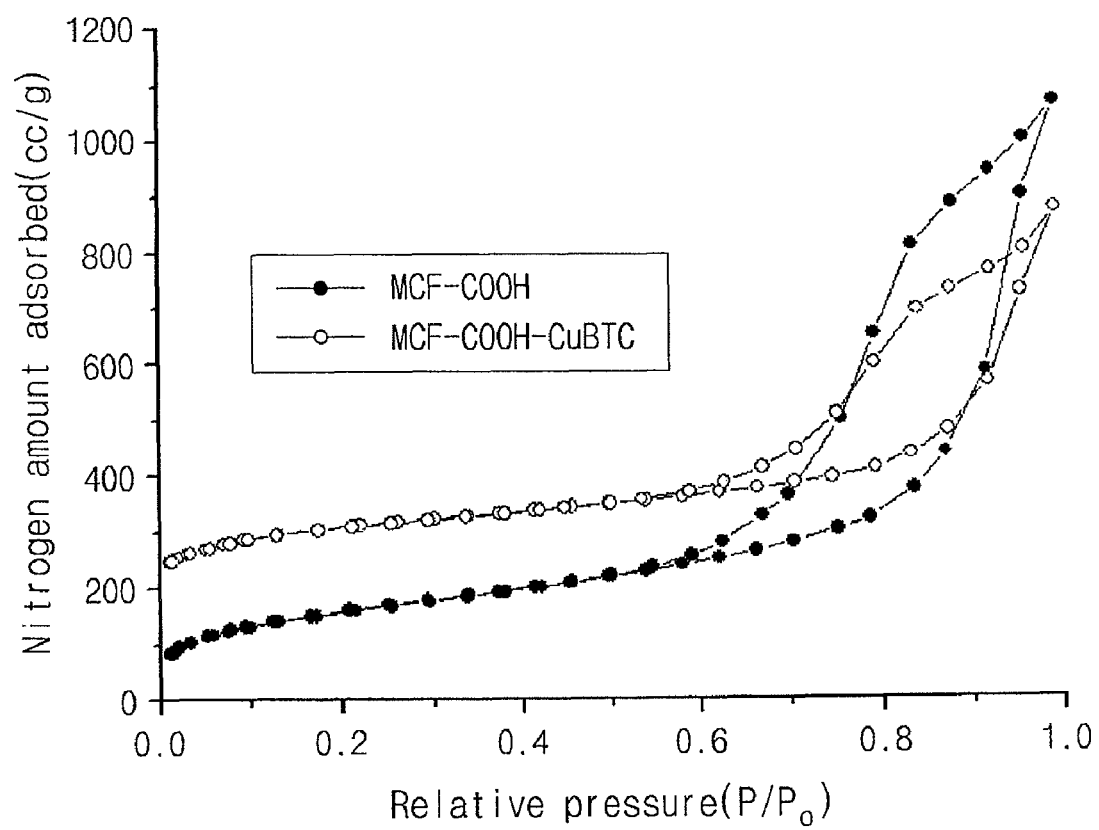

Hereinafter, the present invention will be described in detail.

A precursor solution of a gigantic nanoporous material substituted with organic functional group is prepared as follows. First, sodium silicate ($Na_2Si_3O_7$), serving as a starting material, a pluronic block-copolymer (P123), serving as a surfactant, and triethoxybutylonitrile, serving as an organic substitution group are dissolved in an acetic acid solution, which is a weak acidic solution, and then stirred at a temperature of 60° C. to form a mixture. Subsequently, the mixture is hydrothermally synthesized at a temperature of 100 for 12 hours to prepare an MCF-R ($R_1$ is a primary organic functional group), such as MCF-CN, etc. Subsequently, in order to remove the pluronic polymer (P123) from the prepared MCF-CN and to oxidize the primary organic functional group, such as a cyano (CN) group, etc., the MCF-CN is put into sulfuric acid and then stirred at a temperature of 95° C. for 1 day to synthesize MCF-$CO_2H$, which is a gigantic mesoporous material substituted with a secondary organic functional group ($R_2$). In this case, the MCF-$CO_2H$ may be synthesized using electromagnetic waves, such as microwaves, etc., in addition to the conventional hydrothermal synthesis. Subsequently, the prepared MCF-$CO_2H$ is put into an ethanol solution in which a copper precursor and 1,3,5-benzenetricarboxylic acid (BTC) are dissolved, and then irradiated with ultrasonic waves to form a mixture. Thereafter, the mixture is put into a hydrothermal reactor and then heated by microwaves or an electric heater, so that the MCF-$CO_2H$, which is a gigantic nanoporous material, is hybridized with $Cu_3(BTC)_2$, which is an organic-inorganic porous framework structure through covalent bond, thereby producing a novel MCF-$CO_2H$—$Cu_3(BTC)_2$ (hereinafter, represented by 'MCF-$CO_2H$—CuBTC') nanoporous hybrids.

Accordingly, the covalent bonded nanoporous composite is produced by the steps of 1) mixing an organic precursor for introducing a primary organic functional group, an inorganic precursor and a surfactant to form a mixture and then reacting the mixture to prepare a mesoporous cellular foam (MCF-R) where R is selected from a R1, a primary organic functional group or a R2, a secondary organic functional group; 2) mixing the MCF-R with a solution of a metal-organic framework (MOF) precursor and a nonporous organic-inorganic hybrid (NOIH) precursor to prepare an MCF-R-MOF composite; and 3) crystallizing the MCF-R-MOF composite.

The inorganic precursor may be selected from among silicon (Si), aluminum (Al) and combinations thereof, or may be silicon substituted with Al, Fe, Co, V, Cr, Mn, Ti, Ga, Sn, Zr, Y, La such that the amount thereof is 0~30 mole %, preferably 0.1~10 mole %. Specifically, the inorganic precursor may include one or more transition metals selected from among Ti, Fe, Co, V, Cr, Mn, Ti, Ga, Sn, Zr and Y; and one or more lanthanide metals selected from among Ce, La and combinations thereof or one or more alkoxides. Further, the inorganic precursor may be selected from transition metals, such as Ti, Ni, Fe and Co, and anthanide metals, in addition to Si and Al.

The organic precursor for introducing the primary organic functional group may be prepared using phosphoric acid ($H_3PO_4$) or organosilane compounds represented by Chemical Formulae 1 to 4 below:

  [Chemical Formula 1]

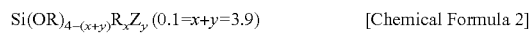  [Chemical Formula 2]

  [Chemical Formula 3]

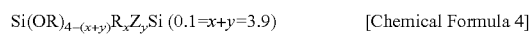  [Chemical Formula 4]

wherein Z is a halogen atom, and R is a substitution group selected from the group consisting of an alkyl group of 1 to 20 carbon atoms, preferably 3 to 7 carbon atoms, the alkyl group being non-substituted or substituted with the halogen atom, an alkenyl group, an alkynyl group, a vinyl group, an amino group, an cyano group, and a mercapto group.

The inorganic precursor and organic precursor may be used such that the ratio of inorganic precursor to organic precursor is 1~50, preferably 10~30. When the ratio of inorganic precursor to organic precursor is less than 1, it is difficult to form a gigantic nanoporous material, and when the ratio of inorganic precursor to organic precursor is more than 50, the number of organic groups that can be bonded with crystalline organic-inorganic hybrids is insufficient. The secondary organic functional group, such as —$CO_2H$, etc., may be formed by oxidizing the primary organic functional group (—CN) with inorganic acids, such as sulfuric acid and the like, or hydrogen peroxide water. Examples of the secondary organic functional group may include —$CO_2H$, —$SO_3H$, and the like. The MCF may be functionalized using each or all of the primary and secondary organic functional groups.

As the surfactant used in the present invention, a cationic, anionic or pluronic surfactant $(EO)_x(PO)_y(EO)_x$, 20<x<120, 20<y<120) may be used. The amount of the surfactant may be 1~10 parts by weight based on 100 parts by weight of the mixed solution. In particular, Preferred examples of the surfactant may include Pluronic P123 (molecular weight 5750 and manufactured by BASF Corp.) and Pluronic F127 (molecular weight 12600, manufactured by BASF Corp.), each of which is an Ethylene Oxide/Propylene Oxide Block Copolymer.

As metals constituting the metal-organic framework (MOF) precursor and non-porous organic-inorganic hybrid (NOIH) precursor, any metal can be used, and preferably, transition metals which can easily form coordination compounds can be used. Specifically, the metal precursor of the metal-organic framework (MOF) or the nonporous organic-inorganic hybrid (NOIH) includes one or more compounds of metals selected from the group consisting of period IV transition metals including Ti, V, Cr, Mn, Fe, Co, Ni, Cu and Zn; period V transition metals including Y, Zr, Nb, Mo, Tc, Ru, Rh, Pd, Ag and Cd; period VI transition metals including Lu, Hf, Ta, W, Re, Os, Ir, Pt, Au and Hg; typical elements including magnesium (Mg), lithium (Li), aluminum (Al) and silicon (Si); and lanthanide metals including lanthanum (La), cerium (Ce) and a mixture thereof. In particular, among the transition metals, chromium (Cr), vanadium (V), iron (Fe), nickel (Ni), cobalt (Co), copper (Cu), titanium (Ti) and manganese (Mn) can be suitably used. In addition to the transition metals, both typical elements forming coordination compounds and lanthanide rare-earth metals can also be used as the metal precursor. Among the typical elements, magnesium (Mg), lithium (Li), aluminum (Al) and silicon (Si) can be suitably used, and, among the lanthanide rare-earth metals, cerium (Ce) and lanthanum (La) can be suitably used. As a metal source, metal compounds as well as pure metals may be used.

An organic ligand, which is a constituent of the organic-inorganic hybrid precursor, is referred to as a linker. Any organic matter having coordination sites, such as $-CO_2^-$, $-CS_2^-$, $-SO_3^-$ and $-N$, may be used as the organic ligand. In order to obtain a stable organic-inorganic hybrid, it is advantageous that organic matter having two or more coordination sites, such as a bidentate ligand or a tridentate ligand, is used. Cationic organic matter as well as neutral organic matter (bipyridine, pyrazine, etc.) and anionic organic matter (carboxylic acid anions, such as terephthalate anions, glutarate anions) can be used as the organic matter, as long as they have coordination sites. Examples of the carboxylic acid anions may include terephthalate anions having an aromatic ring, formate anions having a linear structure, and cyclohexyldicarboxylate anions having a non-aromatic ring. As the organic ligand, in addition to the organic matter having coordination sites, organic matter which can be converted into the matter having coordination sites by reaction can be used. For example, even when an organic acid, such as terephthalic acid, is used, the terephthalic acid is converted into terephthalate after reaction, and the terephthalate can be bonded with metals. Typical Examples of the organic ligand may include organic acids, such as benzenedicarboxylic acid, naphthalenedicarboxylic acid, benzenetricarboxylic acid, naphthalenedicarboxylic acid, pyridinedicarboxylic acid, bipyridyldicarboxylic acid, formic acid, oxalic acid, malonic acid, succinic acid, glutaric acid, hexanedicarboxylic acid and heptanedicarboxylic acid, and anions thereof; pyrazine; bipyridine; and mixtures thereof.

Further, the MCF-R may be mixed with the metal-organic framework (MOF) precursor using an ultrasonic method, an electromagnetic method, or a reflux method.

Finally, the MCF-R-MOF composite may be crystallized using an electric heating method, an ultrasonic method, an electromagnetic method or an electrochemical method.

In order to evaluate the gas storage capacity of the produced novel ultraporous organic-inorganic nanoporous composite, it was put into a high pressure sample holder and then pretreated at a temperature of 200° C. for 6 hours under a vacuum atmosphere (10 torr), and then the amounts of hydrogen adsorbed on the ultraporous organic-inorganic nanoporous composite were measured at 298K and 77K using VTI-100, respectively. Further, the ultraporous organic-inorganic nanoporous to composite may be formed into a powdered or pelleted adsorbent, membrane or separating film and then may be used as a material for selectively adsorbing and separating gases. In particular, the ultraporous organic-inorganic nanoporous hybrids can selectively store and separate hydrogen, oxygen, nitrogen, argon, methane and carbon dioxide. Moreover, the ultraporous organic-inorganic nanoporous hybrids can separate olefin from paraffin such as ethane/ethene, propane/propylene, butane/butene, butane/isobutene etc.

Hereinafter, the present invention will be described in detail with reference to the following Examples. However, the scope of the present invention is not limited thereto.

EXAMPLE 1

Preparation of Gigantic Mesoporous Cellular Foam (MCF-CO$_2$H)

Figure 2:
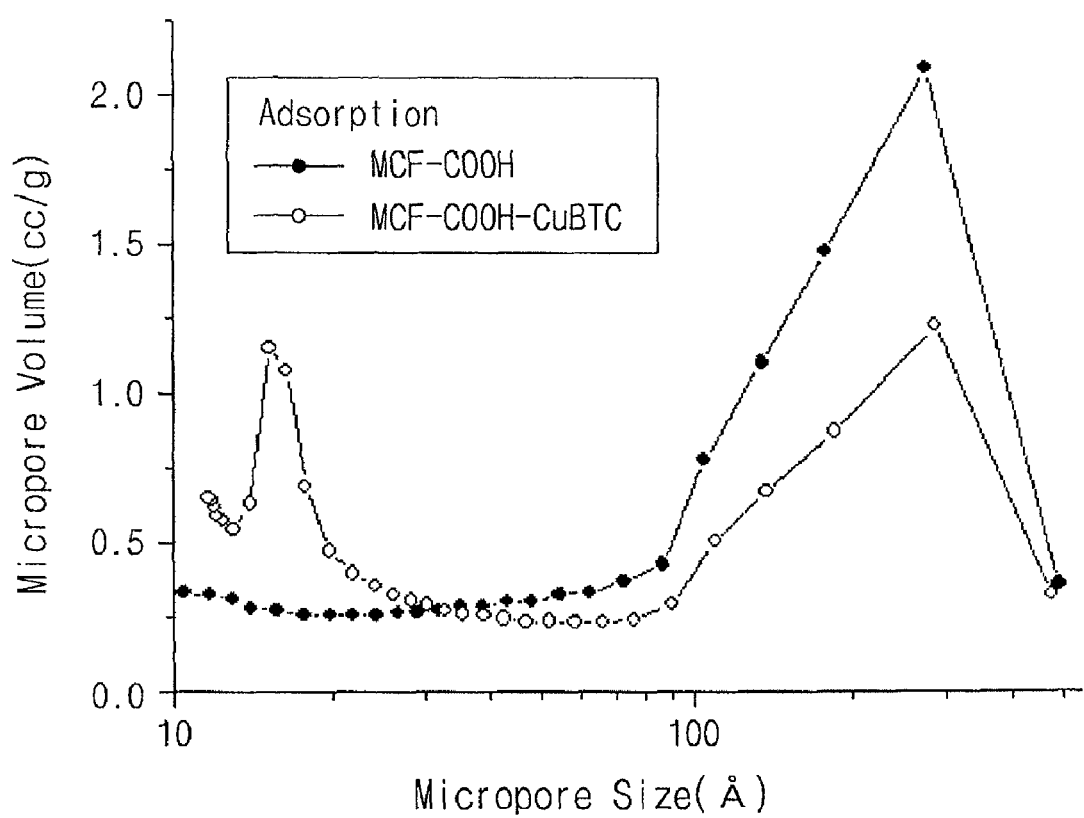
FIG. 2 is a graph showing pore volumes of nanoporous materials prepared in Examples 1 and 6.
Figure 3:
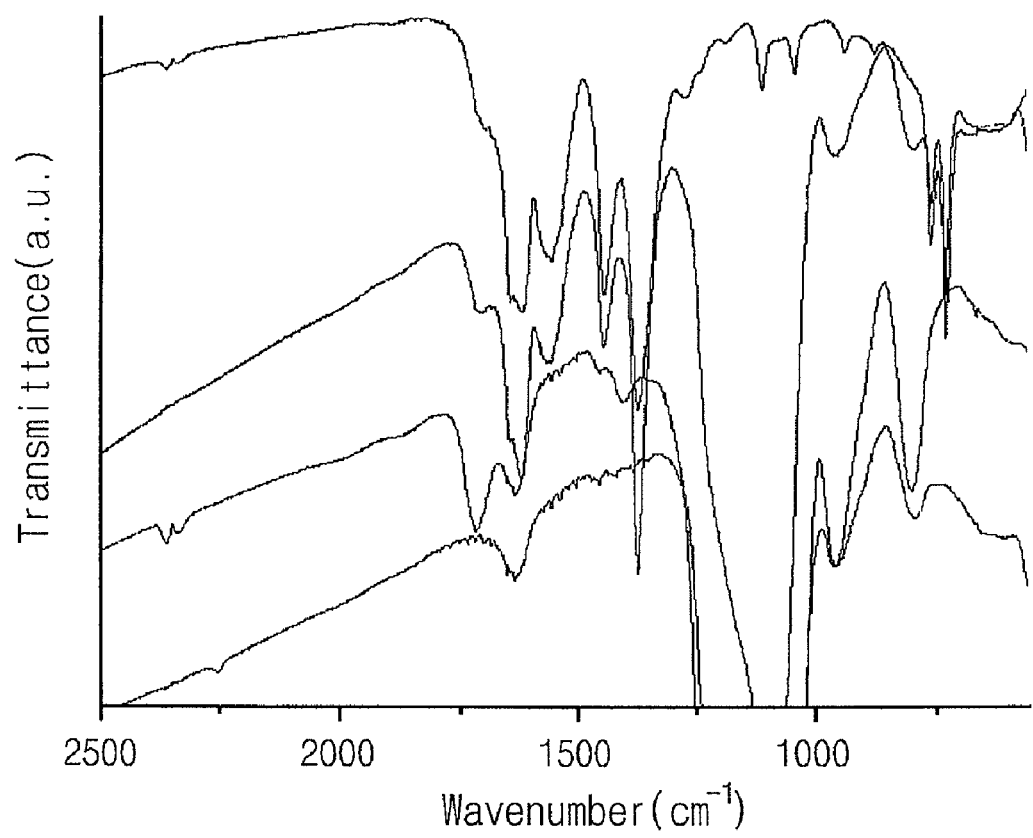
FIG. 3 is a graph showing infrared spectra of nanoporous materials prepared in Examples 1 and 6 and Comparative Example 1.

1.62 g of P123 (molecular weight 5200, manufactured by Aldrich Corp.) and 0.8 g of acetic acid (99%) were dissolved in 33.33 g of water to form a first solution, and then the first solution was heated to a temperature of 60° C. Simultaneously, 0.23 g of sodium silicate (Na$_2$Si$_3$O$_7$) containing 27% of SiO$_2$ and 2.67 g of triethoxybutyronitrile (TEBN) were completely dissolved in 33.33 mL of water to form a second solution. Subsequently, the two solutions were mixed and then stirred at a temperature of 60° C. for 1 hour to form a mixed solution. Thereafter, the mixed solution was hydrothermally synthesized at a temperature of 100° C. for 12 hours to prepare MCF-CN. In order to remove P123 from the prepared MCF-CN and to oxidize a CN group of the MCF-CN, 1 g of the MCF-CN was mixed with 120 mL of sulfuric acid (48%) and then stirred at a temperature of 95° C. for 1 day to prepare a gigantic mesoporous cellular foam (MCF-CO$_2$H). From the hydrogen adsorption curves shown in FIG. 1 and the pore distribution shown in FIG. 2, it can be seen that the prepared mesoporous cellular foam (MCF-CO$_2$H) had a surface area of 578 m$^2$/g and a pore volume of 1.66 mL/g. Further, from the infrared spectra shown in FIG. 3, it can be seen that the mesoporous cellular foam (MCF-CO$_2$H) was formed by oxidizing the MCF-CN with sulfuric acid.

EXAMPLE 2

Preparation of Gigantic Mesoporous Cellular Foam (MCF-NH$_2$)

A gigantic mesoporous cellular foam (MCF-NH$_2$) was prepared using 0.28 g of aminopropyltriethoxysilane (APTES) instead of triethoxybutyronitrile (TEBN) which is a starting material of Example 1. From the infrared absorption peak in a wavenumber range of about 3200~3400 cm$^{-1}$, it can be seen that an amino group was derived from MCF-NH$_2$.

EXAMPLE 3

Preparation of Gigantic Mesoporous Cellular Foam (MCF-SO$_3$H)

A gigantic mesoporous cellular foam (MCF-SH) was prepared using 0.27 g of mercaptopropyltriethoxysilane (MPTES) instead of triethoxybutyronitrile EBN) which is a starting material of Example 1. In order to remove P123 from the prepared MCF-SH and to oxidize an —SH group of the MCF-SH, 1 g of the MCF-SH was mixed with 30 mL of hydrogen peroxide water (28%) and then stirred at a temperature of 50° C. for 6 hours to prepare a gigantic mesoporous cellular foam (MCF-SO$_3$H). From the infrared absorption peak in a wavenumber range of about 1200~1400 cm$^{-1}$, it can be seen that a sulfonic group was derived from MCF-SO$_3$H.

EXAMPLE 4

Preparation of Gigantic TiO$_2$-containing Mesoporous Cellular Foam (Ti-MCF-CO$_2$H)

A gigantic TiO$_2$-containing mesoporous cellular foam (Ti-MCF-CO$_2$H) was prepared using similar method to that of Example 1. The TiO$_2$-containing mesoporous cellular foam (Ti-MCF-CO$_2$H) was prepared as follows. 1.62 g of P123 (molecular weight 5200, manufactured by Aldrich Corp.) and 0.8 g of acetic acid (99%) were dissolved in 33.33 g of water to form a first solution, and then the first solution was heated to a temperature of 60° C. Simultaneously, 3.4 g of titanium iso-butoxide was completely dissolved in 33.33 mL of ethanol to form a second solution. Subsequently, the two solutions were mixed and then stirred at a temperature of 60° C. for 1 hour to form a mixed solution. Thereafter, the mixed solution was hydrothermally synthesized at a temperature of 100° C. for 12 hours and then calcined at a temperature of 500° C. to prepare Ti-MCF. Subsequently, 1 g of the Ti-MCF and 0.23 g of triethoxybutyronitrile (TEBN) were mixed in 0.43 g of toluene and then refluxed to prepare Ti-MCF-CN. In order to oxidize a CN group of the Ti-MCF-CN, 1 g of the Ti-MCF-CN was mixed with 120 mL of sulfuric acid (48%) and then stirred at a temperature of 95° C. for 1 day to prepare a gigantic mesoporous cellular foam (Ti-MCF-CO$_2$H).

EXAMPLE 5

Preparation of Gigantic ZrO$_2$-containing Mesoporous Cellular Foam (Zr-MCF-CO$_2$H)

A gigantic ZrO$_2$-containing mesoporous cellular foam (Zr-MCF-CO$_2$H) was prepared using similar method to that of Example 2. The ZrO$_2$-containing mesoporous cellular foam (Zr-MCF-CO$_2$H) was prepared as follows. 1.62 g of P123 (molecular weight 5200, manufactured by Aldrich Corp.) and 0.8 g of acetic acid (99%) were dissolved in 33.33 g of water to form a first solution, and then the first solution was heated to a temperature of 60° C. Simultaneously, 2.67 g of sodium silicate (Na$_2$Si$_3$O$_7$) containing 27% of SiO$_2$, 0.23 g of triethoxybutyronitrile (TEBN) and 0.92 g of zirconium ethoxide were completely dissolved in 33.33 mL of water to form a second solution. Here, the molar ratio of zirconium to silicon was 0.1~10. Subsequently, the two solutions were mixed and then stirred at a temperature of 60° C. for 1 hour to form a mixed solution. Thereafter, the mixed solution was hydrothermally synthesized at a temperature of 100° C. for 12 hours to prepare Zr-MCF. Subsequently, 1 g of the Zr-MCF and 0.23 g of triethoxybutyronitrile (TEBN) were mixed in 0.43 g of toluene and then refluxed to prepare Zr-MCF-CN. In order to remove P123 from the Zr-MCF-CN and to oxidize a CN group of the Zr-MCF-CN, 1 g of the Zr-MCF-CN was mixed with 120 mL of sulfuric acid (48%) and then stirred at a temperature of 95° C. for 1 day to prepare a gigantic mesoporous cellular foam (Zr-MCF-CO$_2$H).

EXAMPLE 6

Synthesis of Organic-inorganic Nanoporous Hybrids (MCF-CO$_2$—Cu-BTC)

Figure 4:
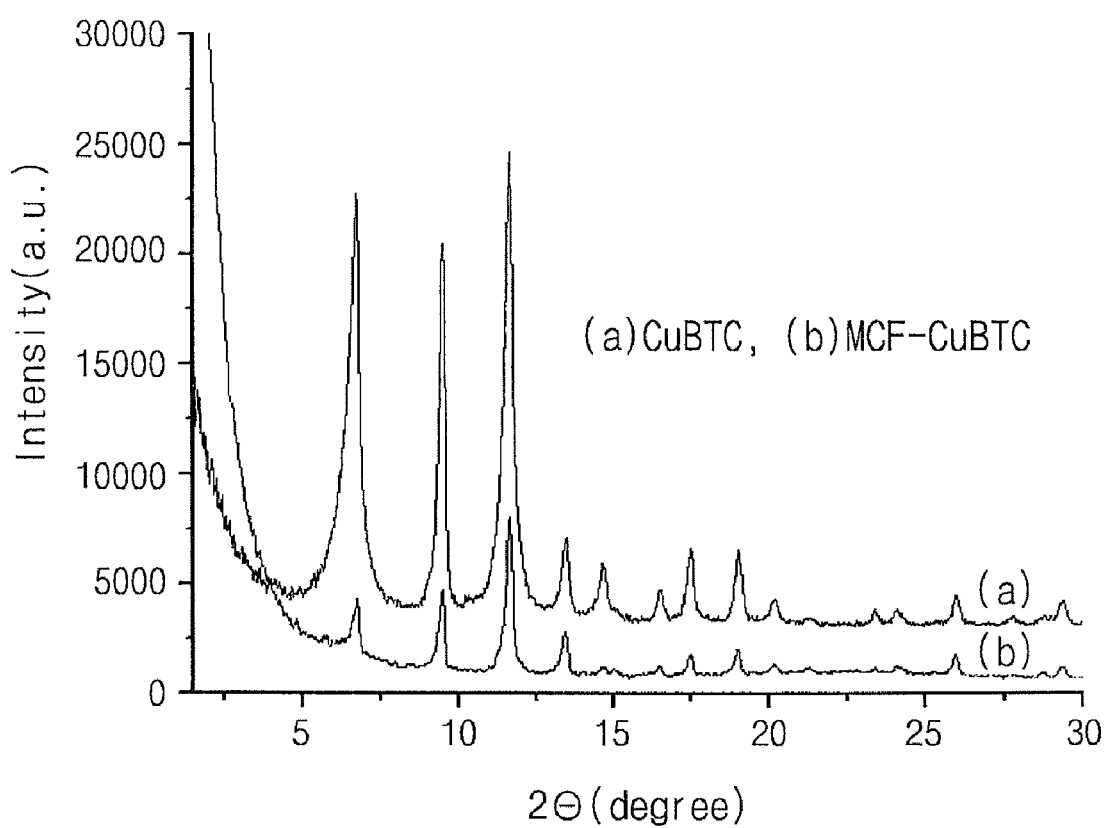
FIG. 4 is a graph showing XRD patterns of nanoporous materials prepared in Examples 1 and 6.

0.2 g of MCF-COOH, prepared in Example 1, and 0.44 g of cupric nitrate.3 hydrate [Cu(NO$_3$)$_2$.3H$_2$O] were mixed with 12 g of water and 12 g of ethanol, and then irradiated with ultrasonic waves for 30 minutes to form a first mixed solution. Subsequently, 0.21 g of 1,3,5-benzeneticarboxylic acid (BTC) was added to the first mixed solution, and then stirred for 10 minutes to form a second mixed solution. Thereafter, the second mixed solution was reacted in a Teflon microwave reactor at a temperature of 140° C. for 30 minutes to produce an organic-inorganic nanoporous composite (MCF-CO$_2$H—Cu-BTC). From the hydrogen adsorption curves shown in FIG. 1 and the pore distribution shown in FIG. 2, it can be seen that the produced organic-inorganic nanoporous composite (MCF-CO$_2$H—Cu-BTC) had a surface area of 1052 m$^2$/g and a pore volume of 1.36 ml/g. The pore volume of the organic-inorganic nanoporous composite (MCF-CO$_2$H—Cu-BTC) was decreased to 18% of that of the mesoporous cellular foam (MCF-CO$_2$H) because Cu-BTC was grown in a —CO$_2$H of MCF-CO$_2$H. Further, from the infrared spectra shown in FIG. 4, it can be seen that the Cu-BTC was formed, and thus distributed in the pores of the MCF-CO$_2$H.

EXAMPLE 7

Synthesis of Organic-inorganic Nanoporous Hybrids (MCF-COO—Fe-MIL-100)

0.2 g of MCF-COOH, prepared in Example 1, and 0.46 g of ferric nitrate.9 hydrate [Fe(NO$_3$)$_3$.9H$_2$O] were mixed with 40 g of water, and then irradiated with ultrasonic waves for 30 minutes to form a first mixed solution. Subsequently, 0.16 g of 1,3,5-benzenetricarboxylic acid (BTC) was added to the first mixed solution, and then stirred for 10 minutes to form a second mixed solution. Thereafter, the second mixed solution was reacted in a Teflon microwave reactor at a temperature of 140° C. for 30 minutes to produce an organic-inorganic nanoporous composite (MCF-CO$_2$H—Fe-MIL-100).

EXAMPLE 8

Synthesis of Organic-inorganic Nanoporous Hybrids (MCF-COO—Cd-BTC)

0.2 g of MCF-COOH, prepared in Example 1, and 0.63 g of cadmium nitrate.4 hydrate [Cd(NO$_3$)$_2$.4H$_2$O] were mixed with 40 g of water, and then irradiated with ultrasonic waves for 30 to minutes to form a first mixed solution. Subsequently, 0.16 g of 1,3,5-benzenetricarboxylic acid (BTC) was added to the first mixed solution, and then stirred for 10 minutes to form a second mixed solution. Thereafter, the second mixed solution was reacted in a Teflon microwave reactor at a temperature of 140° C. for 30 minutes to produce an organic-inorganic nanoporous composite (MCF-CO$_2$H—Cd-BTC).

EXAMPLE 9

Synthesis of Organic-inorganic Nanoporous Hybrids (Ti-MCF-COO—Cu-BTC)

An organic-inorganic nanoporous composite (Ti-MCF-CO$_2$H—Cu-BTC) was produced using 0.2 g of the Ti-MCF-COOH prepared in Example 4 instead of 0.2 g of the MCF-COOH prepared in Example 6.

EXAMPLE 10

Synthesis of Organic-inorganic Nanoporous Hybrids (MCF-COO—Tb-BTC)

0.2 g of MCF-COOH, prepared in Example 1, and 0.49 g of terbium nitrate.5 hydrate [Tb(NO$_3$)$_3$.5H$_2$O] were mixed with 8.4 mL of cyclohexanol and 8.4 mL of water, and then irradiated with ultrasonic waves for 30 minutes to form a first mixed solution. Subsequently, 0.50 g of 1,3,5-benzenetribenzoate (BTB) and 0.8 g of sodium hydroxide (NaOH) were added to the first mixed solution, and then stirred for 10 minutes to form a second mixed solution. Thereafter, the second mixed solution was reacted in a Teflon microwave reactor at a temperature of 100° C. for 30 minutes to produce an organic-inorganic nanoporous composite (MCF-CO$_2$H—Tb-BTB). As the result of XRD analysis of the produced MCF-CO$_2$H—Tb-BTB, it was found that the structure of Tb-BTB in the MCF-CO$_2$H—Tb-BTB was the same as that of MIL-103 disclosed in the document [J. Am. Chem. Soc. 2005, 127, 12788].

EXAMPLE 11

Synthesis of Organic-inorganic Nanoporous Hybrid (MCF-Ni—CPO)

0.914 g of Ni(CH$_3$COO)$_2$.4H$_2$O was dissolved in 12 g of ethanol and 3 g of water. 0.6 g of CH$_3$-MCF-COOH was added into Copper nitrate solution. The ethanol were slowly vaporized at 60° C. Above steps are repeated for 3 times and then product (CH$_3$-MCF-COOH—Cu$^{2+}$) was dried at 80° C. for 12 h. After that, 0.364 g of 2,5-dihydroxyterephthalic acid (DH-TPA) were dissolved in 24 g of ethanol and the added CH$_3$-MCF-COOH—Ni$^{2+}$. The mixed solution was stirred for 5 min at RT and then moved to MW oven followed microwave-irradiation at 110° C. for 30 min. The solid product was filtered with mixed solution of water and ethanol. For the comparison study, pure MCF was treated under same condition with Ni salt and BTC ligands.

COMPARATIVE EXAMPLE 1

Organic-inorganic Porous Material (Cu-BTC)

Cupric nitrate.3 hydrate (Cu(NO$_3$)$_2$3H$_2$O) and 1,3,5-benzenetricarboxylic acid (BTC) were mixed with distilled water and ethanol, as solvents, in a Teflon reactor such that the molar ration of Cu:BTC:ethanol:H$_2$O is 1:0.56:55.6:186. Subsequently, the mixture was irradiated with ultrasonic waves and then pre-treated for 5 minutes to make the mixture uniform and to easily form nuclei. Subsequently, the Teflon reactor including the pre-treated mixture was installed in a microwave reactor (Model: Mars-5, manufactured by CEM Corp.), and then irradiated with microwaves of 2.45 GHz for 2 minutes to be heated to 140° C. Thereafter, the heated mixture was reacted for 30 minutes while the temperature thereof being maintained at 140° C., cooled to room temperature, and then filtered using a paper filter to produce an organic-inorganic porous compound (Cu$_3$(BTC)$_2$) having a cubic crystal structure. As the result of XRD analysis of the produced organic-inorganic porous compound (Cu$_3$(BTC)$_2$), it was found that the organic-inorganic porous compound (Cu$_3$(BTC)$_2$) had a surface area of 1400 m$^2$/g and a pore volume of 0.8 ml/g. Further, it was found that the structure of Cu$_3$(BTC)$_2$ was the same as that of HKUST-1(Cu-BTC) disclosed in the document [Chui. *Science*, 283, 1148 (1999)].

EXPERIMENTAL EXAMPLE 1

Figure 5A:
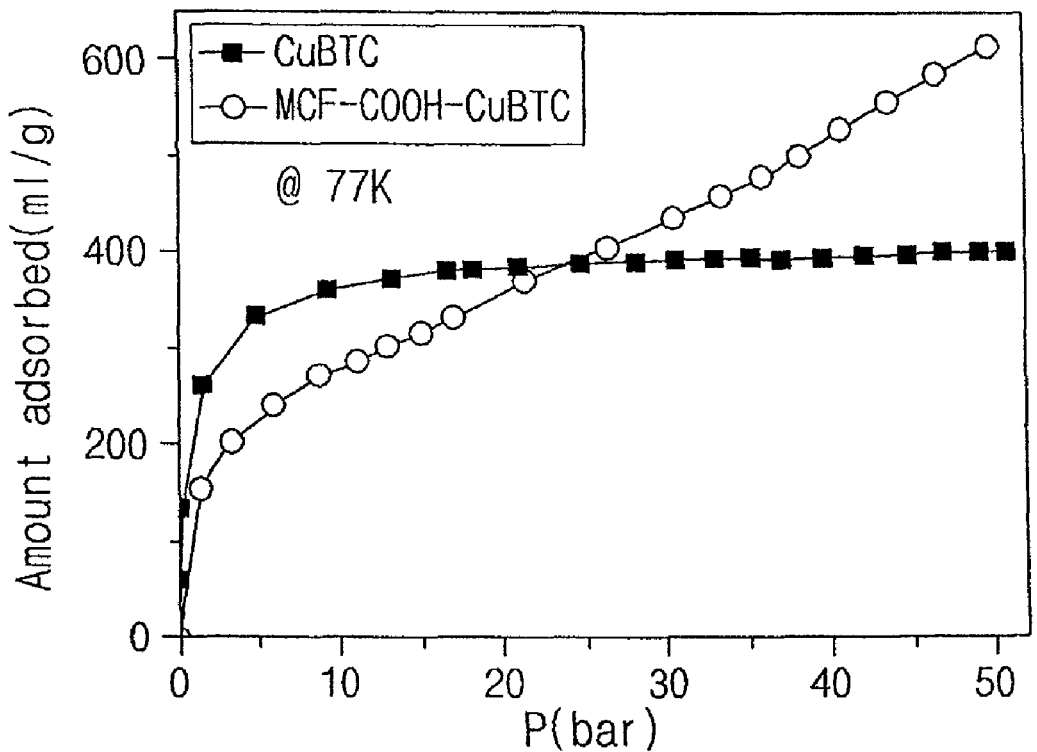
FIG. 5 is a graph showing high-pressure hydrogen adsorption isothermal curves of nanoporous materials prepared in Example 2 and Comparative Example 1.
Figure 5B:
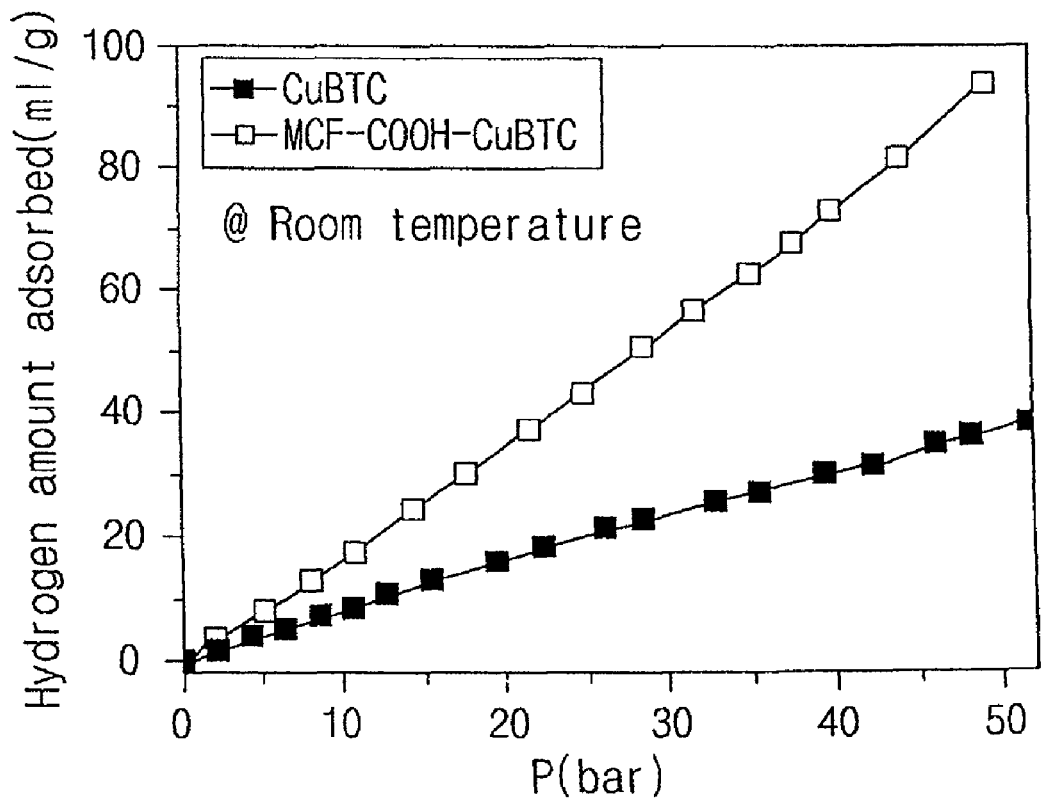

H$_2$ Gas Adsorption Experiment 0.15 g of MCF-COOH—Cu-BTC prepared in Example 2 and 0.15 g of Cu-BTC prepared in Comparative Example 1 were put into a high-pressure sample holder and then pre-treated at a temperature of 200° C. for 6 hours under a vacuum atmosphere (10$^{-5}$ torr), and then the hydrogen adsorption capacities of the MCF-COOH—Cu-BTC and Cu-BTC were measured at 298 K and 77 K using VTI-100, respectively. As the result of adsorbing hydrogen on the MCF-COOH—Cu-BTC and Cu-BTC at a pressure of 50 atms and a temperature of 77 K, it was found that the amount of hydrogen adsorbed in the MCF-CO$_2$H—CuBTC (5.48 wt %) was 1.5 times more than the amount of hydrogen adsorbed in the Cu-BTC (3.6 wt %). In particular, as shown in FIG. 5, the amount of hydrogen adsorbed in the MCF-CO$_2$H—CuBTC at room temperature was 0.83 wt %, and the amount of hydrogen adsorbed in the Cu-BTC at room temperature was 0.34 wt %. Therefore, the amount of hydrogen adsorbed in the MCF-CO$_2$H—CuBTC at room temperature was 2.4 times more than the amount of hydrogen adsorbed in the Cu-BTC (3.6 wt %) at room temperature.

EXPERIMENTAL EXAMPLE 2

Propylene and Propane Sorption Experiments

Figure 6A:
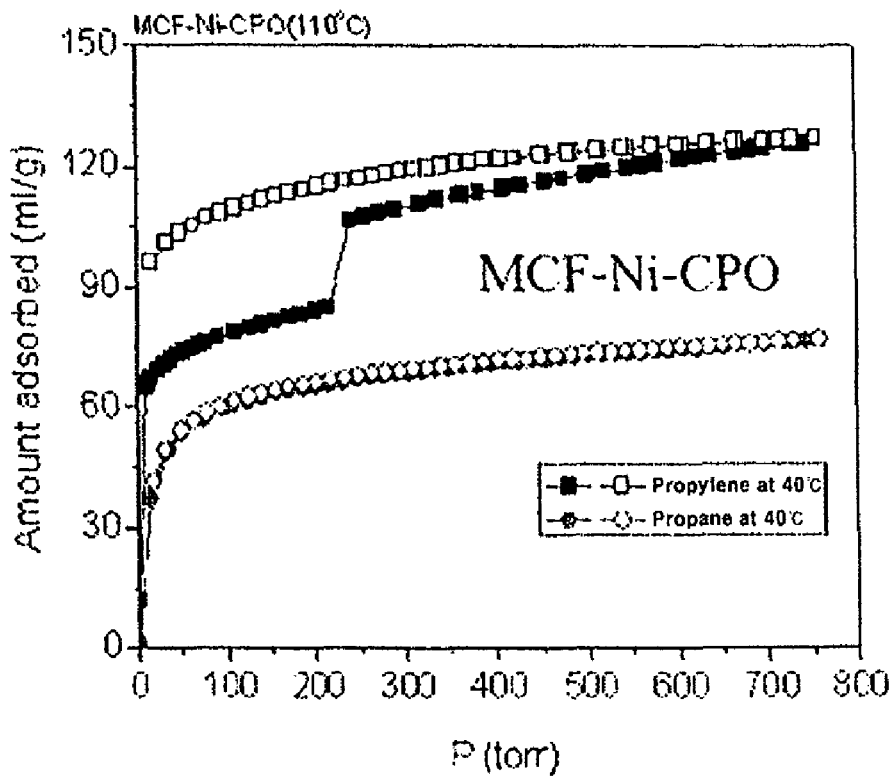
FIG. 6 is a graph showing Propylene and proane adsorption-desorption isothermal curves of nanoporous materials prepared in Example 11((a) on MCF-Ni—CPO, (b) on MCF).
Figure 6B:
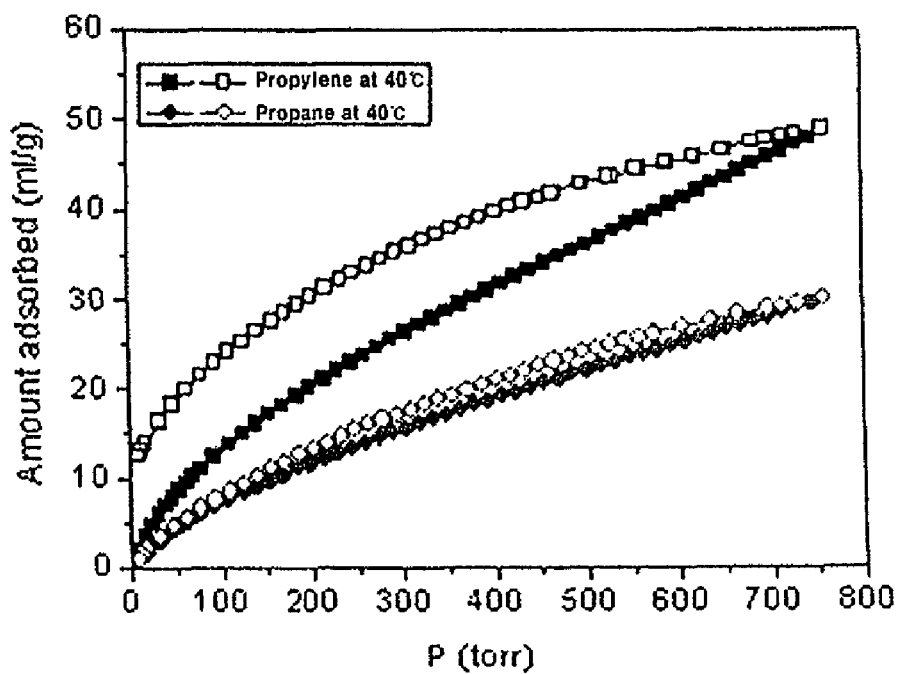

Gas sorption experiments at 40° C. were performed in a glass vacuum manifold equipped with a diffusion pump. Standard volumetric technique was used to obtain the sorption data of small gas molecules in the pressure range from 5 to 760 Torr. Before gas sorption experiments, MCF-Ni—CPO Hybrids of 0.3 g and MCF was slowly (1 K/min) activated by heating from room temperature to the 250° C. for 12 h under vacuum (<10$^{-5}$ Torr). Highly pure gases were used for the sorption measurements. Desorption isotherms were obtained by decreasing the pressure after adsorption at ~760 Torr. The propylene and propane adsorption-desorption isotherms at 40° C. are compared in FIG. 6. The amount of propylene absorbed into MCF-Ni—CPO (79 ml/g) was 6.0 times more than amount of propylene adsorbed in the MCF itself (13 ml/g) at 100 torr.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. Ultraporous organic-inorganic nanoporous hybrids in which a mesoporous material including organic groups on the surface thereof is covalently-bonded with a crystalline organic-inorganic hybrid, the composite produced by the steps of:
   1) mixing an organic precursor for introducing a primary organic functional group, an inorganic precursor and a surfactant to form a mixture and then reacting the mixture to prepare a mesoporous cellular foam (MCF-R) where R is selected from a R1, a primary organic functional group or a R2, a secondary organic functional group;
   2) mixing the MCF-R with a solution of a metal-organic framework (MOF) precursor and a nonporous organic-inorganic hybrid (NOIH) precursor to prepare an MCF-R-MOF composite; and
   3) crystallizing the MCF-R-MOF composite.

2. The ultraporous organic-inorganic nanoporous composite according to claim 1, wherein the inorganic precursor includes one or more of a salt or an alkoxide composed of a typical element selected from among silicon (Si), aluminum (Al) and combinations thereof; and a salt or an alkoxide composed of a metal selected from among transition metals and lanthanide metals.

3. The ultraporous organic-inorganic nanoporous composite according to claim 2, wherein the inorganic precursor includes one or more of a salt or an alkoxide composed of Si; and a salt or an alkoxide composed of a metal capable of being substituted with Si and selected from transition metals selected from among Ti, Fe, Co, V, Cr, Mn, Ti, Ga, Sn, Zr and Y and lanthanide metals selected from among Ce, La and combinations thereof.

4. The ultraporous organic-inorganic nanoporous composite according to claim 1, wherein the organic precursor for introducing the primary organic functional group is prepared using phosphoric acid ($H_3PO_4$) or organosilane compounds represented by Chemical Formulae 1 to 4 below:

$Si(OR)_{4-x}R_x$ (0.1=x=3)  [Chemical Formula 1]

$Si(OR)_{4-(x+y)}R_xZ_y$ (0.1=x+y=3.9)  [Chemical Formula 2]

$Si(OR)_{4-x}R_xSi$ (0.1=x=3)  [Chemical Formula 3]

$Si(OR)_{4-(x+y)}R_xZ_ySi$ (0.1=x+y=3.9)  [Chemical Formula 4]

wherein Z is a halogen atom, and R is a substitution group selected from the group consisting of an alkyl group of 1 to 20 carbon atoms, the alkyl group being unsubstituted or substituted with the halogen atom, an alkenyl group, an alkynyl group, a vinyl group, an amino group, an cyano group, and a mercapto group.

5. The ultraporous organic-inorganic nanoporous composite according to claim 1, wherein a metal precursor of the metal-organic framework (MOF) or the nonporous organic-inorganic hybrid (NOIH) includes one or more compounds of metals selected from the group consisting of period IV transition metals including Ti, V, Cr, Mn, Fe, Co, Ni, Cu and Zn; period V transition metals including Y, Zr, Nb, Mo, Tc, Ru, Rh, Pd, Ag and Cd; period VI transition metals including Lu, Hf, Ta, W, Re, Os, Ir, Pt, Au and Hg; typical elements including magnesium (Mg), lithium (Li), aluminum (Al) and silicon (Si); and lanthanide metals including lanthanum (La), cerium (Ce) and a mixture thereof.

6. The ultraporous organic-inorganic nanoporous composite according to claim 1, wherein the organic-inorganic hybrid includes an organic ligand selected from the group consisting of —$CO_2^-$, —$CS_2^-$, —$SO_3^-$ and —N, the organic ligand having coordination sites.

7. The ultraporous organic-inorganic nanoporous composite according to claim 6, wherein the organic ligand is a compound including multiple carboxylic acid, multiple carboxylic acid anions, pyridine, imidazolate, or pyrazine.

8. The ultraporous organic-inorganic nanoporous composite according to claim 7, wherein the multiple carboxylic acid includes benzenedicarboxylic acid, naphthalenedicarboxylic acid, benzenetricarboxylic acid, naphthalenetricarboxylic acid, pyridinedicarboxylic acid, bipyridyldicarboxylic acid, formic acid, oxalic acid, malonic acid, succinic acid, glutaric acid, hexanedicarboxylic acid, or heptanedicarboxylic acid.

9. The ultraporous organic-inorganic nanoporous composite according to claim 1, wherein the MCF-R is mixed with the metal-organic framework (MOF) precursor using an ultrasonic method, an electromagnetic method, or a reflux method.

10. The ultraporous organic-inorganic nanoporous composite according to claim 1, wherein the MCF-R-MOF composite is crystallized using an electric heating method, an ultrasonic method, an electromagnetic method or an electrochemical method.

11. A method of separating and storing gas, wherein the ultraporous organic-inorganic nanoporous composite according to claim 1 is formed into a powdered or molded adsorbent, membrane or separating film and then used.

12. The method of separating and storing gas according to claim 11 wherein the gas is hydrogen, oxygen, nitrogen, argon, methane, carbon dioxide or olefin/paraffin mixed gas.

13. The method of separating and storing gas according to claim 11, wherein the gas is an olefin/paraffin mixed gas selected from the group consisting of ethane/ethene, propane/propylene, butane/butene and butane/isobutene mixtures.

14. A method of producing an ultraporous organic-inorganic nanoporous composite, comprising:
1) mixing an organic precursor for introducing a primary organic functional group, an inorganic precursor, a surfactant and acetic acid to form a mixture and then reacting the mixture to prepare a mesoporous cellular foam (MCF-R) where R is selected from a R1, a primary organic functional group or a R2, a secondary organic functional group;
2) mixing the MCF-R with a solution of a metal-organic framework (MOF) precursor and a nonporous organic-inorganic hybrid (NOIH) precursor to prepare an MCF-R-MOF composite; and
3) crystallizing the MCF-R-MOF composite.

* * * * *